United States Patent [19]
Kanayama et al.

[11] Patent Number: 5,103,680
[45] Date of Patent: Apr. 14, 1992

[54] METHOD OF TESTING SPLIT CERAMIC ALIGNMENT SLEEVE AND APPARATUS THEREFOR

[75] Inventors: Kazunori Kanayama, Tokyo; Etsuji Sugita, Tachikawa; Ryo Nagase; Shin'ichi Iwano, both of Mito, all of Japan

[73] Assignee: Nippon Telegraph and Telephone Corporation, Tokyo, Japan

[21] Appl. No.: 628,642

[22] Filed: Dec. 12, 1990

[30] Foreign Application Priority Data

Dec. 14, 1989 [JP] Japan .................................. 1-322741

[51] Int. Cl.⁵ .............................................. G01N 3/20
[52] U.S. Cl. ...................................................... 73/849
[58] Field of Search ........................... 73/849, 851, 799

[56] References Cited
FOREIGN PATENT DOCUMENTS
777547 11/1980 U.S.S.R. ................................. 73/849

OTHER PUBLICATIONS
Doroshenko, P. A. et al., Method of Determining . . . Alloys, Ind. Lab (U.S.A.), vol. 43, No. 3, (Publ. Sep. 1977), pp. 427-429.

Primary Examiner—Jerry W. Myracle
Attorney, Agent, or Firm—Julian Cohen

[57] ABSTRACT

A cylindrical split alignment sleeve of ceramic material has an axial slit and is used in an optical fiber connector for connecting optical fibers to each other. In order to establish the strength reliability of the split ceramic alignment sleeve, a predetermined stress is applied to it by a test procedure ensuring no damage to the sleeve. According to the invention, a test load is applied to the inner circumferential surface of the split ceramic alignment sleeve by a loading part which includes stationary and movable members having inclined slidable contact surfaces. The sleeve is applied onto the load part and the movable member is displaced to apply load to the sleeve. The magnitude of load can be detected by deformation of the loading part or by displacement of the movable member.

7 Claims, 7 Drawing Sheets

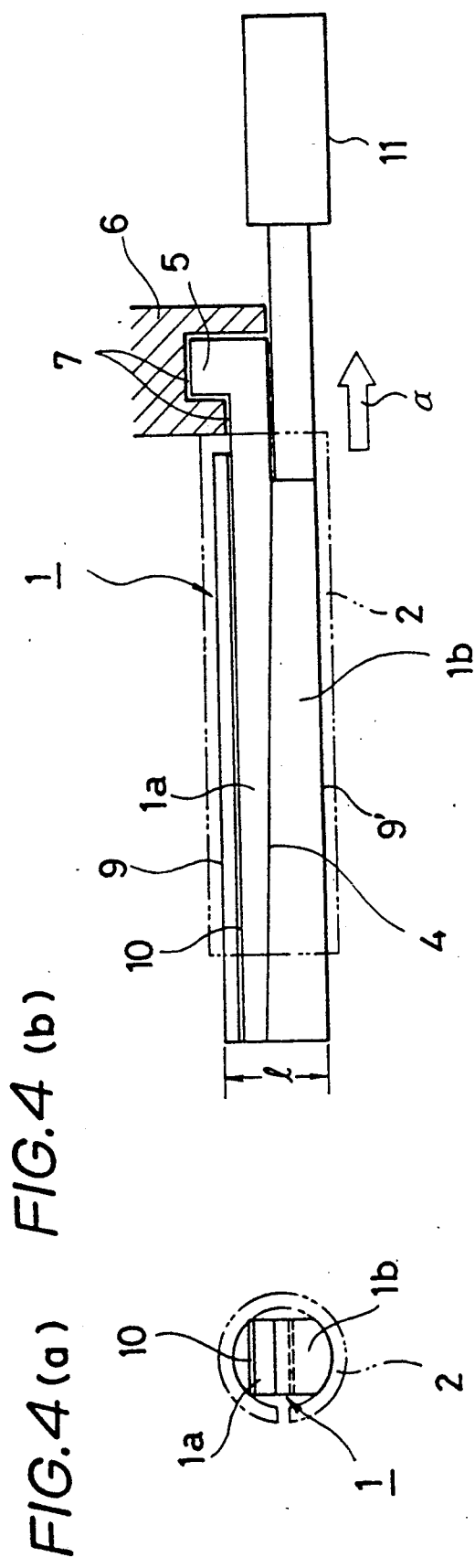

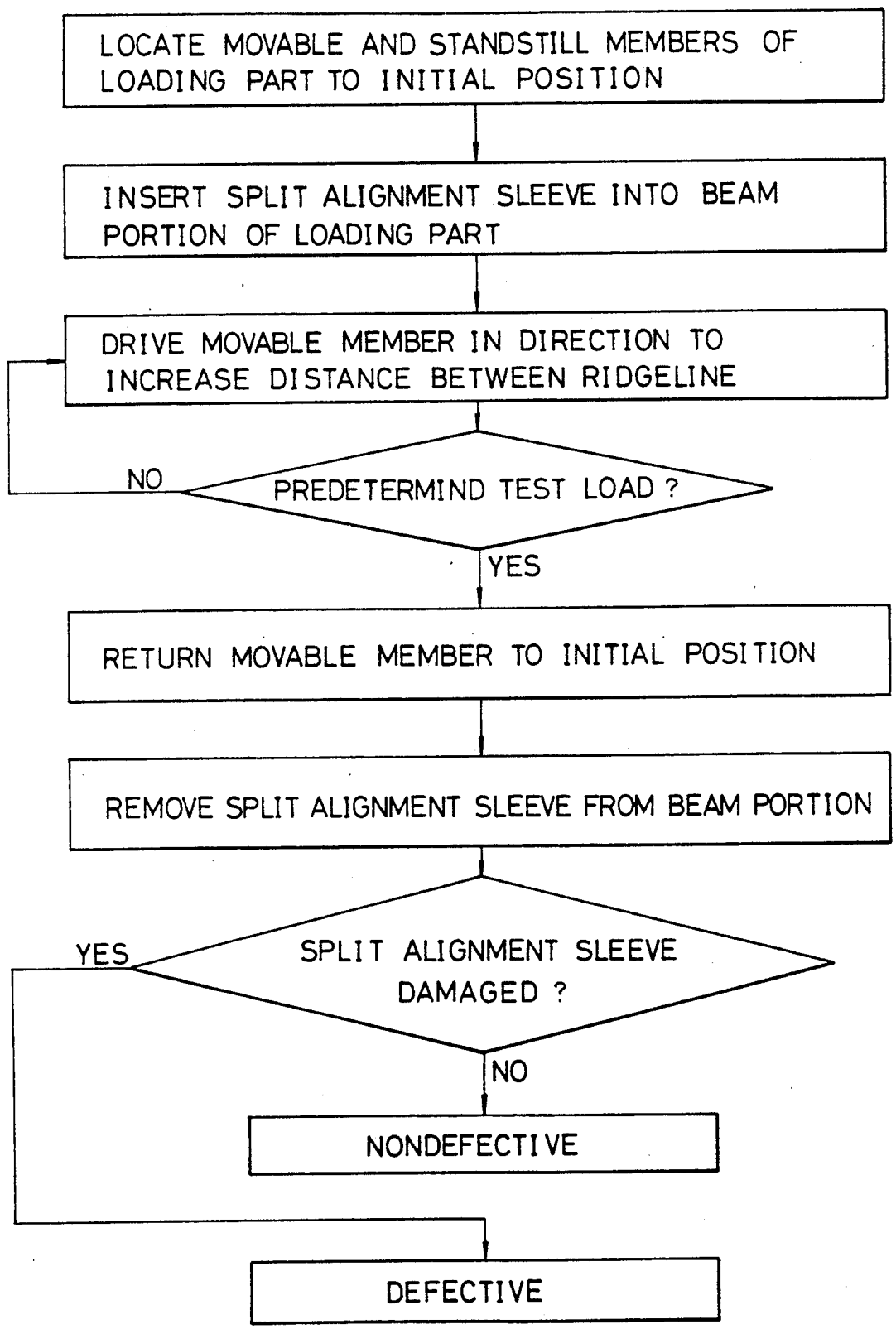

METHOD OF TESTING SPLIT CERAMIC ALIGNMENT SLEEVE AND APPARATUS THEREFOR

BACKGROUND OF THE INVENTION

1. Field of the Invention

The present invention relates to a method of testing a split ceramic alignment sleeve used in an optical fiber connector used in optical fiber communications and an apparatus therefor.

2. Description of Prior Art

A typical conventional optical fiber connector has a well-known structure in which an optical fiber is fixed at the center of a solid cylindrical ferrule, the resultant assembly is fitted in a hollow cylindrical alignment sleeve having an accurate inner diameter, and end faces of the ferrules are aligned with and abut against each other.

The most popular alignment sleeve used in the above optical fiber connector is a split alignment sleeve having a slit in an axial direction of the solid cylindrical ferrule. A typical example of the conventional split alignment sleeve is made of phosphor bronze. However, split ceramic alignment sleeves are also manufactured. In particular, a split zirconia ceramic alignment sleeve having the same material as a zirconia ferrule is used in a connection of the zirconia ceramic ferrules having mating portions made of zirconia ceramics. It is known that more stable connection characteristics than those obtained by using the split phosphor bronze alignment sleeve can be obtained (JAP-PAT-KOKAI NO. 33110/1990).

The following conventional method is known for evaluating a defective/nondefective split ceramic alignment sleeve before it is used in an optical fiber connector.

First of all, flaw detection of a split alignment sleeve is generally performed as quality control in the manufacture. More specifically, a flaw on the surface of a split alignment sleeve is dyed with a dyestuff, and the presence/absence of a flaw is visually checked. This method is called a color check method. Alternatively, light from a light source is transmitted through a split alignment sleeve to check the presence/absence of the flaw. In these test methods, a quantitative test of split ceramic alignment sleeves cannot be performed.

A load test method capable of applying a specific mechanical load on each split alignment sleeve to perform a quantitative test for the life of split ceramic alignment sleeves, which test has been rarely satisfactorily performed by the conventional flaw detection methods, is disclosed (JAP-PAT-KOKAI NO. 231545/1990).

FIG. 1 shows a test method in which L-shaped upper and lower loading parts A and B are inserted into a slit 3 of a split ceramic alignment sleeve 2 and test loads are applied to the L-shaped upper and lower loading parts A and B to open the slit 3. FIG. 2 shows another test method in which test loads are applied to flat upper and lower loading parts C and D so as to clamp the split ceramic alignment sleeve 2.

These load test methods can quantitatively perform a test of split ceramic alignment sleeves and can supply highly reliable split ceramic alignment sleeves. Regardless of these advantages, the method relying on a tensile strength test tool, as shown in FIG. 1, requires cumbersome operations for attaching the L-shaped upper and lower loading parts A and B into the slit 3 or detaching them from the slit 3, thus degrading operability. In addition, the size of the slit 3 is small, and excessive loads act on the L-shaped upper and lower loading parts A and B to test a high-strength member such as a split ceramic alignment sleeve, thus causing damage to the loading parts A and B. In the method shown in FIG. 2, tensile stresses act on the peripheral portions of the split alignment sleeve 2. This method is not suitable as a test method of a split alignment sleeve generally used to receive tensile stress on the inner circumferential surface of split alignment sleeve 2.

SUMMARY OF THE INVENTION

It is therefore an object of the present invention to provide a highly reliable method of testing a split ceramic alignment sleeve so as to easily provide lifetime proof.

It is another object of the present invention to provide a test method capable of easily performing a test of a split ceramic alignment sleeve.

DISCLOSURE OF THE INVENTION

A split alignment sleeve is used in an optical fiber connector for connecting optical fibers to each other. When the split alignment sleeve is made of a ceramic material, characteristics of the optical fiber connector can be greatly improved. However, a split ceramic alignment sleeve is a brittle material, its quality must be established by a reliable test prior to use in an optical fiber connector.

It is an object of the present invention to provide a highly reliable method of testing a split ceramic alignment sleeve so as to easily ensure lifetime proof and to provide a test apparatus therefor.

In order to achieve the above object of the present invention, there is provided a test method comprising the steps of:

(1) locating a movable member and a stationary member of a loading part of a test apparatus for applying a test load on a split ceramic alignment sleeve at an initial position;

(2) inserting the split ceramic alignment sleeve to be tested into a beam portion of the loading part of the test apparatus;

(3) moving the movable member of the loading part of the test apparatus to apply a predetermined test load on the split ceramic alignment sleeve;

(4) returning the movable member of the loading part of the test apparatus to the initial position;

(5) removing the split ceramic alignment sleeve from the beam portion of the loading part of the test apparatus;

(6) determining whether the split ceramic alignment sleeve is damaged by the test load.

The split ceramic alignment sleeve is tested by the above steps (1) to (6).

In the test apparatus, the shape of the loading part inserted into the split ceramic alignment sleeve to apply the load thereon is divided into at least the movable member and the stationary member by sliding contact surfaces which are in slidable contact with each other along an extended direction. The loading part has a cantilevered structure whose one end is a free end. The loading part has ridgelines at farthest diagonal positions of an outer circumferential portion, and these ridgelines are parallel to each other along the extended direction. The distance between the ridgelines is smaller than the inner diameter of the split ceramic alignment sleeve. The sliding contact surfaces of the movable and stationary members are located between the ridgelines and are constituted by inclined surfaces along the extended direction.

The movable or stationary member of the loading part is moved along the inclined surfaces in the extended direction, so that the distance between the ridgelines is increased or decreased. Therefore, a test load can be applied to the split ceramic alignment sleeve.

A piezoelectric device or a dielectric sandwiched between electrodes is attached on the stationary member. The test load can be detected by this piezoelectric device or dielectric.

BRIEF DESCRIPTION OF THE DRAWINGS

FIGS. 4(a) and 4(b) are views showing the first embodiment of a test apparatus used in a test of a split ceramic alignment sleeve according to the present invention;

FIG. 9 is a flow chart showing a proof test sequence of a split ceramic alignment sleeve according to the present invention.

BEST MODE OF CARRYING OUT THE INVENTION

The present invention will be described in detail with reference to the accompanying drawings.

Figure 1:
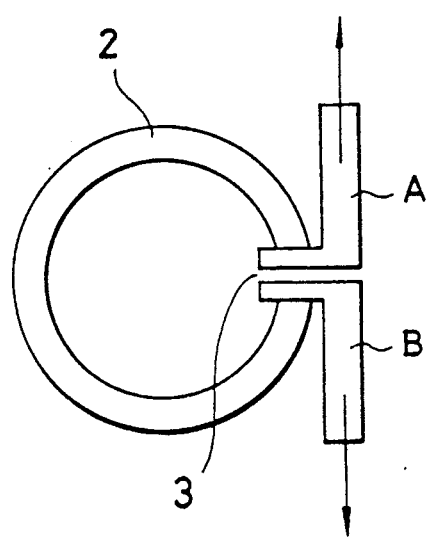
FIG. 1 is a view showing a conventional method of testing a split ceramic alignment sleeve, wherein test loads are applied to increase the size of a slit.
Figure 2:
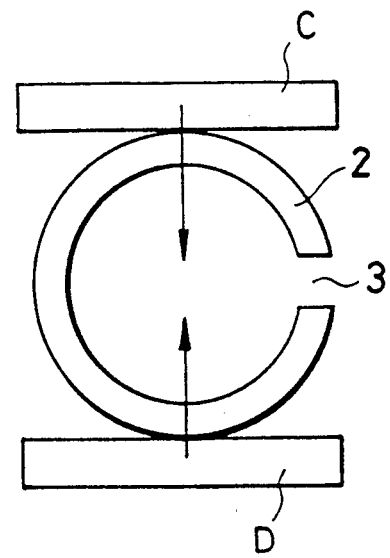
FIG. 2 is a view showing another conventional method of testing a split ceramic alignment sleeve, wherein test loads are applied to compress the split alignment sleeve.
Figure 3:
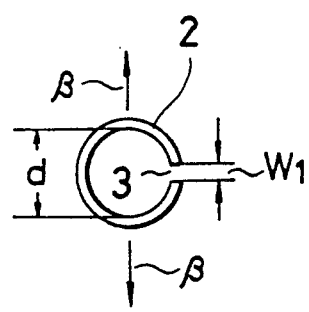
FIGS. 3(a) and 3(b) are views showing a structure of a split ceramic alignment sleeve.
Figure 3:
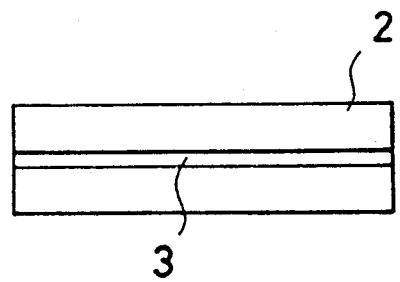

FIGS. 3(a) and 3(b) are views showing the structure of a split ceramic alignment sleeve, in which FIG. 3(a) is a front view thereof, and FIG. 3(b) is a side view thereof. A split alignment sleeve 2 has a slit 3 having a width $W_1$, and its inner diameter is d.

First Embodiment

Figures 5A, 5B:
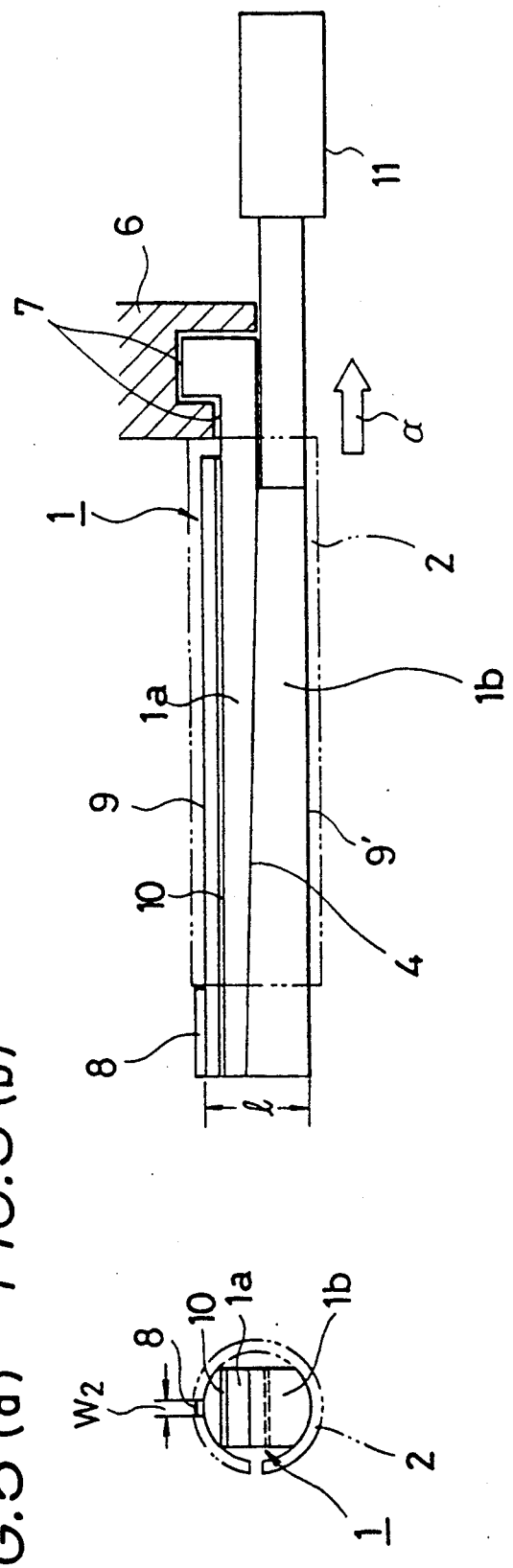
FIGS. 5(a) and 5(b) are views showing the second embodiment of a test apparatus used in a test of a split ceramic alignment sleeve according to the present invention.

FIGS. 4(a) and 4(b) show an arrangement of a split ceramic alignment sleeve test apparatus according to the first embodiment of the present invention, in which FIG. 4(a) is a front view thereof, and FIG. 5(b) is a partially cutaway side view thereof. Referring to FIGS. 4(a) and 4(b), reference numeral 1 denotes a loading part divided into an upper stationary member 1a and a lower movable member 1b. The movable and stationary members are in contact with each other along inclined surfaces 4 descending to the lower right in the longitudinal direction of the loading part 1. The upper stationary member 1a is fixedly held in a holder 6 by a projection 5, and a clearance 7 is present between the projection 5 and the holder 6. The upper stationary member 1a can be vertically moved with respect to the holder 6 secured to upper stationary member 1a is a piezoelectric device 10 which overlies the inclined surfaces 4, and the piezoelectric device 10 extends in a direction perpendicular to planes having farthest parallel ridgelines 9 and 9' of the loading part 1. The lower movable member 1b is connected to an actuator 11 and can be moved in a horizontal direction indicated by $\alpha$. In the state shown in FIGS. 4(a) and 4(b), the distance l between the ridgelines 9 and 9' is slightly smaller than the inner diameter of the split alignment sleeve 2 shown in FIGS. 3(a) and 3(b).

The method of testing the split ceramic alignment sleeve 2 by using the test method of the first embodiment will be described below.

The split alignment sleeve 2 is fitted on the loading part 1. Since a relationship between the distance l between the ridgelines 9 and 9' of the loading part 1 and the inner diameter d of the split alignment sleeve 2 is given by l < d, the split alignment sleeve can be easily fitted on the loading part 1.

The actuator 11 is actuated to produce a displacement $\alpha$ to the lower movable member 1b in the direction indicated by an arrow in FIG. 4(b). The lower movable member 1b is slid along the inclined surface 4 of the upper stationary member 1a, so that the upper stationary member 1a is pushed upward by the inclined surface 4 of the movable member 1b. At this time, since the clearance 7 is formed between the projection 6 and the holder 6, the upper stationary member 1a floats upward to increase the distance between the ridgelines 9 and 9'. When the displacement $\alpha$ is appropriately set, condition l > d is established. A test load $\beta$ (FIG. 3(a)) in a direction to increase the width of the slit 3 is applied through the ridgelines 9 and 9' uniformly in the circumferential and longitudinal directions of the split alignment sleeve 2. Since the piezoelectric element 10 on the upper stationary member 1a is capable of generating a voltage corresponding to a load, the test load $\beta$ can be monitored by measuring the voltage of the piezoelectric device 10 during the test. Therefore, the displacement $\alpha$ can be controlled.

Second Embodiment

FIGS. 5(a) and 5(b) show an arrangement of a split ceramic alignment sleeve test apparatus according to the second embodiment of the present invention, in which FIG. 5(a) is a front view thereof, and FIG. 5(b) is a partially cutaway sectional view thereof. The second embodiment is different from the first embodiment in that upper stationary member 1a has a stop projection 8 at its free end, and the stop projection has a height slightly smaller than the width $W_1$ of the slit 3 of the split alignment sleeve 2. The steps method of testing the split ceramic alignment sleeve 2 by using the test apparatus of the second embodiment are substantially the same as those of the first embodiment, except that the stop projection 8 is fitted in the slit 3 of the split alignment sleeve 2, and the split alignment sleeve 2 is fitted on the loading part 1, the split alignment sleeve 2 is rotated in an extended direction upon passing of the slit 3 over the stop projection 8, and the end face of the split alignment sleeve 2 abuts against the rear end of the stop projection 8, as shown in FIG. 5(b).

The methods of testing the split ceramic alignment sleeves by using the test apparatuses of the first and second embodiments have the following features.

(1) Since a test can be performed by inserting the loading part 1 into the split alignment sleeve 2 and displacing the lower movable member 1b, the test can be simply performed at low cost, and productivity of split ceramic alignment sleeves can be improved.

(2) Since the loading part 1 receives a uniform compression force and a small tension along its longitudinal direction, it is rarely deformed. As compared with conventional methods, a loading portion and a portion for supporting the loading portion need not be increased in size. The test apparatus can be made small at low cost.

(3) Since the piezoelectric device for detecting the load during the test is arranged on the upper stationary member, a test can be performed with high precision.

In the first or second embodiment, it is possible to fix the lower movable member 1b and apply the displacement $\alpha$ to the upper member 1a in a reverse direction by connecting the actuator 11 to the holder 6, to give any front shape to the loading part 1 except for that shown in FIG. 4(a) or 5(a), and to divide the loading part 1 into three or more parts. In addition, the test load $\beta$ is further increased to destroy the split alignment sleeve 2 and to measure the mechanical strength of the split alignment sleeve 2 from the piezoelectric device voltage obtained at the time of destruction.

Third Embodiment

The third embodiment of the present invention will be described below.

Figure 6:
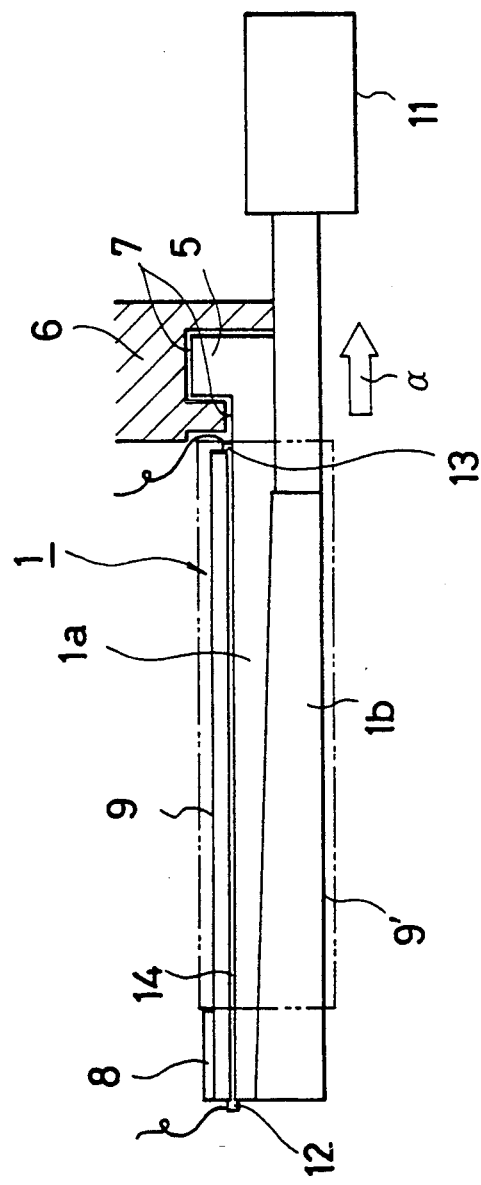
FIG. 6 is a view showing the third embodiment of a test apparatus used in a proof test of a split ceramic alignment sleeve according to the present invention.

FIG. 6 is a partially cutaway sectional side view showing an arrangement of a split ceramic alignment sleeve test apparatus according to the third embodiment. In the third embodiment, a dielectric 14 sandwiched between electrodes 12 and 3 is fixed in place of the piezoelectric element 10 of the second embodiment shown in FIG. 5(b). The reference numerals as in the second embodiment denote the same parts in the third embodiment.

In the third embodiment, a loadreaction reaction acting on a split alignment sleeve 2 acts on the dielectric 14, and the thickness of the dielectric 14 is changed in accordance with this reaction. The electrostatic capacitance between the electrodes 12 and 13 is changed. The electrostatic capacitance of the dielectric 14 is measured to monitor a test load $\beta$ acting on the split alignment sleeve. Other functions in the third embodiment are the same as those of the second embodiment. The same features as in the first or second embodiment can be obtained in the third embodiment.

Fourth Embodiment

The fourth embodiment of the present invention will be described below.

Figures 7A, 7B:
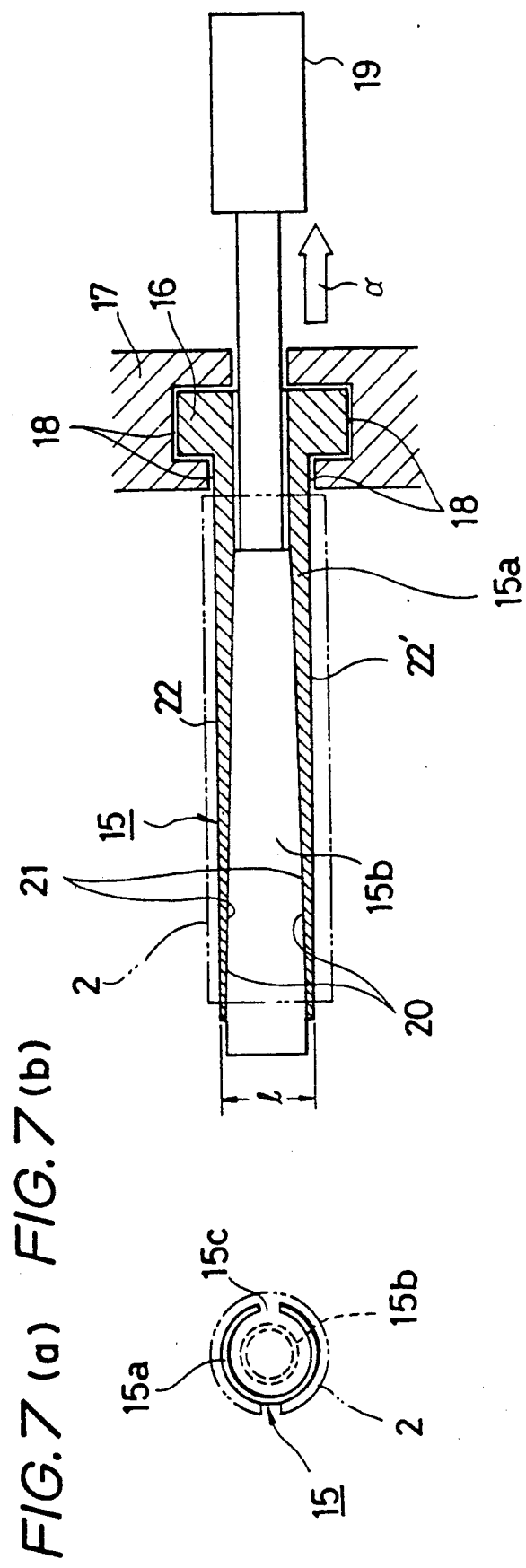
FIGS. 7(a) and 7(b) are views showing the fourth embodiment of a test apparatus used in a proof test of a split ceramic alignment sleeve according to the present invention.

FIGS. 7(a) and 7(b) show an arrangement of a split ceramic alignment sleeve test apparatus according to the fourth embodiment, in which FIG. 7(a) is a front view thereof and FIG. 7(b) is a partially cutaway side view thereof Referring to FIGS. 7(a) and 7(b), reference numeral 15 denotes a loading part for applying a load on a split ceramic alignment sleeve 2. The loading part 15 is divided into an outer stationary member 15a and an inner movable member 15b. The inner circumferential surface of the outer stationary member 15a is frustoconical. The outer stationary member 15a has a cylindrical shape having a slit 15c extending along the longitudinal direction. The outer stationary member 15a is held in holder 17 by a projection 16. A clearance 18 is formed between the projection 16 and the holder 17, and the outer stationary member 15a can be deformed in a direction to open the slit 15c. The inner movable member 15b is a rod-like member having an outer circumferential frustoconical surface, connected to an actuator 19, and moved in a horizontal direction indicated by arrow $\alpha$. The outer stationary member 15a and the inner movable member 15b are in contact with each other through an inclined surface 20 (outer stationary member) as a frustoconical inner circumferential surface and an inclined surface 21 (inner movable member) as an outer circumferential surface. In the state shown in FIG. 7(b), an outer diameter l of the outer member 15a is slightly smaller than the inner diameter d of the split alignment sleeve 2.

A test method of testing the split ceramic alignment sleeve 2 by using the test apparatus according to the fourth embodiment will be described below.

The split alignment sleeve 2 is inserted into the outer stationary member 15a of the loading part 15. At this time, since the relationship between the outer diameter l of the outer stationary member 15a and the inner diameter d of the split alignment sleeve 2 satisfies condition l < d, the split alignment sleeve 2 can be easily inserted into the outer stationary member 15a. The actuator 19 is actuated to impart displacement $\alpha$ to the inner movable member 15b in the direction of an arrow. The inclined surface 21 of the inner movable member 15b and the inclined surface 20 of the outer on member 15a slide each other, and the outer member 15a is deformed in a direction to increase the size of slit 15c, thereby increasing the distance l. When the displacement $\alpha$ is appropriately set as in the first to third embodiments, the outer diameter l of the outer stationary member 15a becomes larger than the inner diameter d of the split alignment sleeve 2 (l < d). A load is applied from ridgelines 22 and 22' of the loading part 15 to increase the size of slit 15c uniformly in the circumferential and longitudinal directions of the split alignment sleeve. Therefore, a test load $\beta$ (FIGS. 3(a) and 3(b)) acts on the split alignment sleeve 2.

A method of testing the split ceramic alignment sleeve 2 using the test apparatus of the fourth embodiment has a feature in which no relative motion between the outer member 15a and the split alignment sleeve 2 is present. In the fourth embodiment, when a piezoelectric device is attached to the outer member 15a, the test load $\beta$ can be monitored. The same effect as in the first or second embodiment can be obtained in the fourth embodiment. In addition, even if the outer member 15a and the inner movable member 15b have a shape other than cylindrical and columnar shapes, the same effect as in the fourth embodiment can be obtained if a given shape has the same function as that of the fourth embodiment.

Fifth Embodiment

The fifth embodiment of the present invention will be described below.

Figure 8:
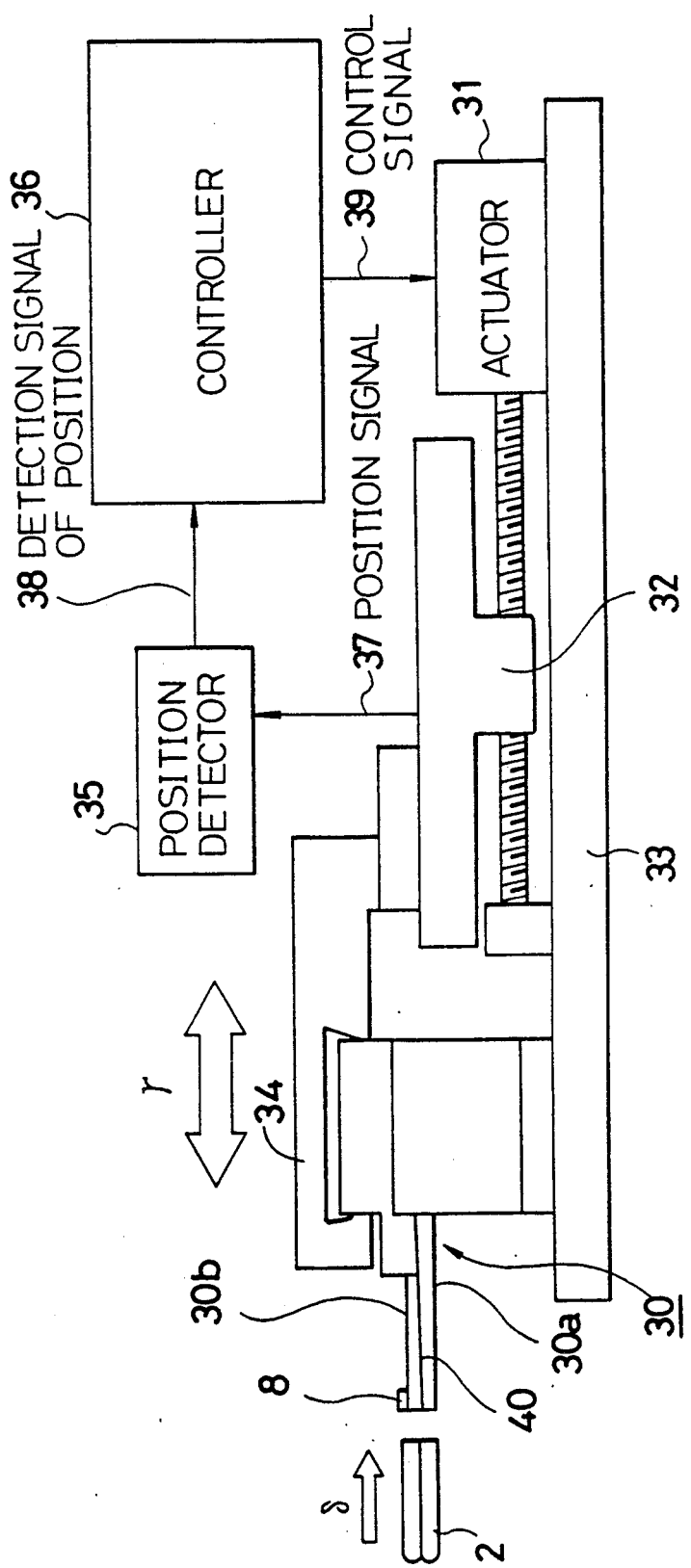
FIG. 8 is a view showing the fifth embodiment of a test apparatus used in a proof test of a split ceramic alignment sleeve according to the present invention.

FIG. 8 shows an arrangement of a split ceramic alignment sleeve test apparatus according to the fifth embodiment. Referring to FIG. 8, reference numeral 30 denotes a loading part for applying a test load to a split ceramic alignment sleeve 2. The loading part 30 comprises a lower stationary member 30a and an upper movable member 30b. The lower stationary member 30a and the upper movable member 30b are in contact through their inclined surfaces 40. Although the upper movable member 30b is held by a holder 34, the upper movable member 30b can be vertically moved and can be moved in a right-and-left direction in accordance with the holder 34. The lower stationary member 30a is fixed on a base 33. The holder 34 is fixed on a guide mechanism 32, and the guide mechanism 32 is connected to an actuator 31. The upper movable member 30b is driven through by a displacement γ by means of the actuator 31 in the right-and-left direction. A position detector 35 detects the position of the right-and-left displacement γ of the guide mechanism 32, and consequently the position of the upper movable member can be detected. A controller 36 controls the operation of the actuator 31 on the basis of a detection signal 38 of position from the position detector 35. More specifically, a control signal 39 is sent to the actuator 31 to control its operation.

Test procedures of the split ceramic alignment sleeve 2 by using the test apparatus of the fifth embodiment will be described below.

The split ceramic alignment sleeve 2 is inserted into the loading part 30. The diameter of the loading part 30 is slightly smaller than the inner diameter d of the split ceramic alignment sleeve 2. In this state, when the actuator 31 is driven by the control signal 39, the upper movable member 30b is driven through the guide mechanism 32 and the holder 34. As in the first to third embodiments, a test load is applied to the split ceramic alignment sleeve 2. In the process wherein the test load is applied, the position signal 37 is input from the guide mechanism 32 to the position detector 35 upon a displacement of the upper movable member 30b, and the position detector 35 sends the detection signal of position to the controller 36. When the controller 36 detects a displacement of the upper movable member 30b corresponding to a predetermined test load, the controller 36 sends the control signal 39 to the actuator 31, thereby stopping the actuator 31. The controller 36 then sends an instruction in the form of the control signal 39 to the actuator 31 to move the upper movable member 30b in a direction to release the test load acting on the split ceramic alignment sleeve 2. The guide mechanism 32 is moved by the actuator 31. When the controller 36 detects through the position detector 36 that the upper movable member 30b returns to a position where the split ceramic alignment sleeve 2 is inserted, the controller 36 sends a control signal to the actuator 31, thereby stopping the actuator 31 and hence completing the test.

Since the test of the split ceramic alignment sleeve by using the test apparatus according to the fifth embodiment can be automatically performed, test efficiency can be improved, and the test cost can be reduced.

It is possible to use any one of the loading parts of the first to fifth embodiments as the loading part of the fifth embodiment, as a matter of course.

Procedures of a test method using the split ceramic alignment sleeve test apparatuses of the first to fifth embodiments will be described below.

FIG. 9 is a flow chart of the procedures of the test method of the split ceramic alignment sleeve of the present invention. The proof test procedures are represented by the following steps.

(1) The movable and stationary members of the loading part are located so that the distance between the parallel ridgelines of the loading part is slightly smaller than the inner diameter of the split ceramic alignment sleeve. At this time, a relative position between the movable and stationary members is defined as an initial position.

(2) The split alignment sleeve is inserted into a portion of the loading part which has a cantilevered structure (i.e., a beam portion) from the free end of the beam portion in the longitudinal direction of the split alignment sleeve until the split alignment sleeve entirely overlaps the beam portion.

(3) The movable member of the loading part is driven to be in slidable contact with the stationary member through the inclined sliding contact surfaces in the longitudinal direction of the beam portion and in a direction to increase the distance between the ridgelines until one of the following conditions is satisfied, i.e., (a) until the piezoelectric device or the dielectric attached to the loading part detects the predetermined test load, and (b) until the split alignment sleeve is enlarged by an amount corresponding to the predetermined test load.

(4) The movable member is returned to the initial position.

(5) The split alignment sleeve is removed from the free end of the beam portion of the loading part in the longitudinal direction of the split alignment sleeve.

(6) A test result is evaluated. The evaluation criterion is given such that the split alignment sleeve will not be damaged during movement of the movable member along the stationary member during the period of time immediately after procedure (1) is started and immediately before procedure (5) is completed.

As described above, since a test method and an apparatus therefor according to the present invention facilitate proof the strength of a split ceramic alignment sleeve by simple procedures, the test efficiency can be improved, and the test cost can be reduced. Since the loading part is not susceptible to deformation and a uniform load acts on the split ceramic alignment sleeve with a simple structure, the test apparatus can be made compact at low cost. Since the test apparatus comprises a device for detecting a load during a test, a highly accurate test can be performed.

The test method and the apparatus therefor according to the present invention are also effective to establish the strength reliability of a C-shaped ceramic ring in addition to split ceramic alignment sleeves.

What is claimed is:

1. A method of testing a cylindrical split alignment sleeve having an axial slit and made of a ceramic material, said split alignment sleeve being used as an optical fiber connection, a predetermined load being applied to the sleeve before said sleeve is used in said optical fiber connector, the quality of said split alignment sleeve being tested on the basis of a criterion which ensures no damage to said split alignment connector upon application of said predetermined load thereto, said method comprising the steps of:

(a) locating movable and stationary members of a loading part in an initial position so that the distance between parallel ridgelines of said loading part is slightly smaller than the inner diameter of said split ceramic alignment sleeve, said loading part being int he form of a beam portion of a cantilevered structure having a fixed end and a free end;

(b) inserting said split alignment sleeve, longitudinally thereof, into a portion of said loading part from the free end of said beam portion until said split alignment sleeve completely overlaps said beam portion;

(c) moving said movable member of said loading part to be in slidable contact with said stationary member through inclined sliding contact surfaces thereof in a longitudinal direction of said beam portion and in a direction to increase the distance between the parallel ridgelines until a predetermined test load acts on said split alignment sleeve;

(d) returning said movable member to the initial position;

(e) removing said split alignment sleeve from said free end of said beam portion of said loading part in the longitudinal direction of said split alignment sleeve; and (f) evaluating a test result.

2. A method as claimed in claim 1 comprising detecting load applied to said split alignment sleeve by detecting deformation of said loading part due to movement of said movable member.

3. A method as claimed in claim 2 comprising detecting load applied to said split alignment sleeve by detecting displacement of said movable member.

4. An apparatus of testing a cylindrical split alignment sleeve made of a ceramic material and having an axial slit, said split alignment sleeve being used for an optical fiber connector in which end faces of said pair of ferrules abut against each other, and wherein a predetermined load is applied to said sleeve before said sleeve is used as an optical fiber connector, and the quality of said split alignment sleeve is tested on the basis criteria which ensure no damage to said split alignment sleeve upon application of said predetermined load thereto, said apparatus comprising a loading part insertable into said split alignment sleeve to apply a predetermined load to said split alignment sleeve, said loading part including a movable member and a stationary member, said members having surfaces in slidable contact with each other in the longitudinal direction of the sleeve, said loading part comprising a cantilevered structure having a free end, said loading part further comprising parallel ridgelines located at farthest diagonal positions on an outer circumferential portion of said loading part and extending in said longitudinal direction, the ridgelines having a spacing therebetween which is less than an inner diameter of said split alignment sleeve, said slidingcontact surfaces being located between the parallel ridgelines and constituted by surfaces inclined with respect to the longitudinal direction of said loading part, one of said members of said loading part having a proximal end cantilevered in a transverse direction, said movable member being longitudinally dispaceable to produce sliding of said inclined surfaces relative to each other.

5. An apparatus according to claim 4, comprising a piezoelectric device is stacked on at least said stationary member of said loading part and extending in a direction perpendicular to planes including the parallel ridgelines.

6. An apparatus according to claim 4, comprising a dielectric member sandwiched between electrodes and disposed on at least said stationary member of said loading part, said dielectric member extending in a direction perpendicular to planes including the parallel ridgelines.

7. An apparatus according to claim 4, further comprising a position detector for detecting a position of said movable member of said loading part, and a controller for controlling displacement of said movable member on the basis of an output signal from said position detector.

* * * * *